United States Patent
Langhals et al.

(10) Patent No.: US 6,335,171 B1
(45) Date of Patent: Jan. 1, 2002

(54) IMMUNOCHEMICAL DETERMINATION OF SUBSTANCES CONTAINED ON TEXTILE FIBERS OR POLYMERS

(75) Inventors: Heinz Langhals, Ottobrunn; Rupert Brosius, München; Bertold Hock, Freising, all of (DE)

(73) Assignee: Diagnostic SYstems Biotechnologie GmbH, Munich (DE)

( * ) Notice: Subject to any disclaimer, the term of this patent is extended or adjusted under 35 U.S.C. 154(b) by 0 days.

(21) Appl. No.: 09/329,488

(22) Filed: Jun. 10, 1999

Related U.S. Application Data

(63) Continuation-in-part of application No. PCT/EP97/06763, filed on Dec. 3, 1997.

(30) Foreign Application Priority Data

Dec. 11, 1996 (DE) .......................................... 196 51 599

(51) Int. Cl.[7] .............................................. G01N 33/53
(52) U.S. Cl. ........................... 435/7.1; 422/56; 422/61; 435/7.9; 435/7.94; 435/287.7; 436/513; 436/518; 436/531; 436/823
(58) Field of Search ...................... 422/56, 61; 435/7.1, 435/7.9, 7.94, 287.7; 436/513, 518, 531, 823

(56) References Cited

U.S. PATENT DOCUMENTS 5,169,757 A * 12/1992 Yamazaki et al.
5,324,642 A   6/1994 Baumgartner ............... 435/7.1
5,840,587 A * 11/1998 Stewart et al.

OTHER PUBLICATIONS

Hemmila, I., Clin. Chem., 31(3):359–370, 1985.*
International Preliminary Examination Report dated Mar. 12, 1999 in PCT/EP97/06763.
"Use of Immunoblot Technique for Detection of Human IgE and IgG antibodies to Individual Silk Proteins", Dewair et al.; J. Allergy Clin. Immunol, Oct. 1985, pp. 537–342.
"Strumpffarben–Allergie", Hausen et al.; Deutsche Medizinische Wochenschrift, 109, Sep. 1984, pp. 1469–1475 (English abstract only).
"Immunoglobulin E Antibodies Against a Reactive Dye" Hagmar et al.; Scand J. Work Environ Health 12 (1986), pp. 221–222.
"Fluorescence Photometric Detection of Sizing Agents", Döbel et al.; Melliand Textilberichte May 1996, pp. 298–300 (with translation).
Journal abstract, Fischer et al., 1990.

* cited by examiner

Primary Examiner—Bao-Thuy L. Nguyen
(74) Attorney, Agent, or Firm—Marshall, O'Toole, Gerstein, Murray & Borun

(57) ABSTRACT

A method for the detection of substances contained on textile fibers or other natural or synthetic polymers is disclosed. The contained substances are identified with immunochemical methods, where the immunochemical reaction can occur on the fiber or polymer. The method is especially suitable for the determination of substances that can act as allergens.

15 Claims, 1 Drawing Sheet

IMMUNOCHEMICAL DETERMINATION OF SUBSTANCES CONTAINED ON TEXTILE FIBERS OR POLYMERS

CROSS-REFERENCE TO RELATED APPLICATION

This is a continuation of International Application No. PCT/EP97/06763 filed Dec. 3, 1997, the disclosure of which is incorporated herein by reference.

BACKGROUND OF THE INVENTION

1. Field of the Invention

The invention is concerned with a method for the detection of substances contained on textile fibers or other natural or synthetic polymers.

2. Description of Related Technology

Textiles or foods, e.g., luxury foods, have numerous substances contained in them which could act as allergens for consumers, depending on immunological disposition. These allergens trigger allergic reactions which are manifested with an extensive symptomatology, mostly by strong release of histamine. Erythema, irritation of mucosa, asthmatic reactions, or even drop in blood pressure with shock-like states may result in allergic persons. Therefore, it is of great importance for allergic persons to identify substances that represent a risk potential according to the particular individual allergic profile in textiles and foods, e.g., luxury foods, etc., with a rapid process that is easy to perform.

U.S. Pat. No. 5,324,642 describes a method for the analysis of an analyte in a keratin structure (e.g., hair, nails), in which an enzyme and a compound with low redox potential are allowed to act on a sample of the keratin structure, in order to degrade the structure and to dissolve the analyte in this digesting solution. The detection of the analyte is preferably done by immunoassay techniques on a protein basis (that is, with antibodies).

In Dewair et al., J. Allergy Clin. Immunol. 76 (4), 537–542 (1985), "Use of immunoblot technique for detection of human IgE and IgG antibodies to individual silk proteins", silk proteins are extracted from silk, separated with the aid of polyacrylamide gel electrophoresis (that is, not with antibodies) and incubated with human serum which may contain IgE- and IgG-antibodies against silk proteins. The detection of the antibodies bound to the silk proteins is carried out using the immunoblot technique.

In B. M. Hausen et al., Deutsche Medizinische Wochenschrift, 109 (39), 1469–1475 (1984), "Hosiery Dye Allergy", it is reported that test persons with hosiery allergy reacted allergically in the epicutaneous test to isolated hosiery dyes (especially azo dyes) separated using chromatography. A detection of the allergens with the antibodies is not described.

SUMMARY OF THE INVENTION

The invention provides a method for detecting or quantitatively determining substances contained in textile fibers and/or other natural or synthetic polymers with the aid of antibodies whereby a consumer can check the allergenic potential of a textile or of a food such as a luxury food before purchasing it.

According to the invention, a substance contained on a textile fiber or polymer substrate is detected by directly contacting a surface of the substrate and the substance contained therein with antibodies that specifically bind to the substance, and detecting or quantitatively determining the antibodies bound to the substance.

BRIEF DESCRIPTION OF THE FIGURES

The invention will be explained in more detail with the aid of the following figures.

DETAILED DESCRIPTION OF THE INVENTION

Figure 1:
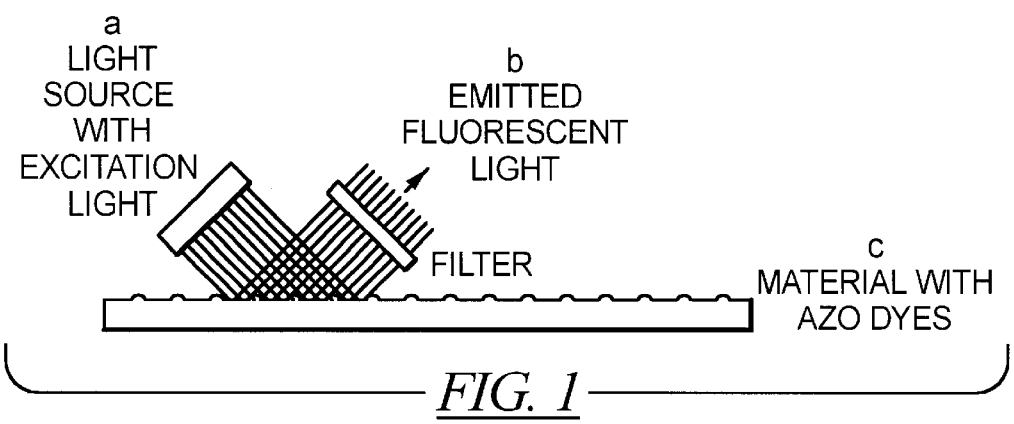
FIG. 1 shows schematically the detection of antibodies with the aid of fluorescent-marked antibodies. For this purpose, irradiation with light of a certain excitation wavelength is introduced. After excitation, the fluorescent markers emit a fluorescent light, which is filtered in order to eliminate nonspecific signals. The fluorescent radiation of the marker molecule can be detected directly.
Figure 2:
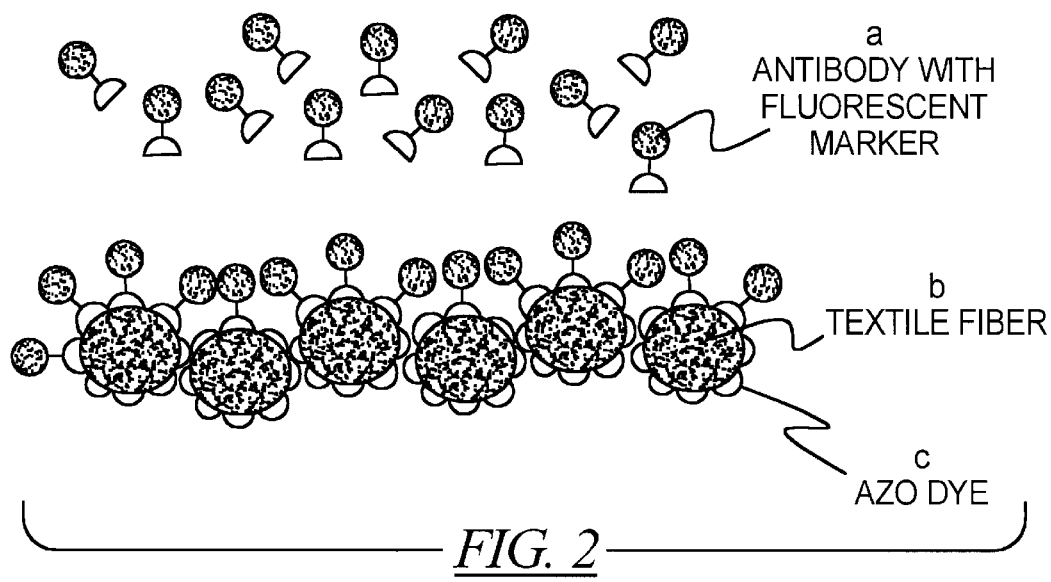
FIG. 2 shows schematically the binding reaction of a specific antibody to an antigen on a textile fiber. In the case shown, this is a fluorescent-marked antibody which is directed against azo dyes. After specific binding of the antibody to the azo dye on the fiber, the detection process can proceed.
Figure 3:
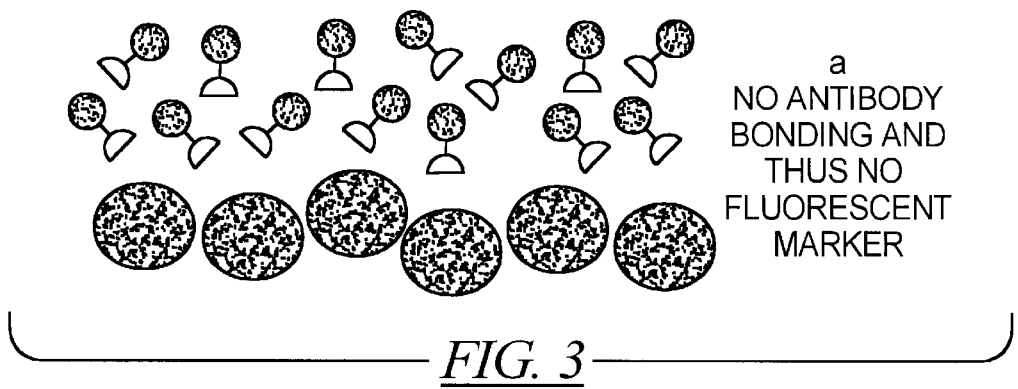
FIG. 3 shows schematically the behavior of the antibodies which do not recognize any epitope on the fiber. In this case, the fluorescence signal of the antibody on the fiber is not produced.

An advantage of the antibodies used for detection according to the invention lies in the fact that they bind not only to dissolved molecules, but also to immobilized structures. This opens up the attractive possibility to determine substances that can act as allergens, directly on the fiber or the polymer. As a result, the expensive desorption or cleavage of the contained substances, which also involves analytical uncertainties, can be eliminated. Therefore, in the invention, the detection reaction is carried out directly on the fibers of a textile or on natural or synthetic polymers, and thus provides direct detection of the potential allergens contained with the aid of a direct determination of the antibodies on the fibers or polymers.

Suitable fiber or polymer materials in which the contained substances can be detected according to the invention include but are not limited to cotton, wool or other animal hair such as horsehair, for example, silk, jute, sisal, hemp or flax and their converted products, for example, viscose fibers, nitrate silk, and copper rayon e.g., REYON fibers, synthetic materials made of polyvinyl chloride, cellulose acetate, polycarbonates, polyamides, polyurethanes, polyimides, polybenzimidazoles, melamine resins, silicones, polyesters, polyethers, polystyrene, polymethyl methacrylate, polyethylene, polypropylene, polyvinyl acetate, polyacrylonitrile, polybutadiene, polychlorobutadiene or polyisoprene and the copolymers of the monomers from which these materials are found, and combinations of the foregoing polymers.

It is preferred to use a nonspecific antibody to saturate the surface of the investigated substrate in order to minimize the nonspecific binding of the specific, detecting antibody. Fibers or polymers possess many nonspecific binding possibilities for the detecting antibody, as a result of which the actual detection reaction may be interfered with. In order to suppress this, it is favorable to saturate the surface of the material to be investigated with antibodies which are not directed against the substance to be detected. Since relatively large amounts of these antibodies are needed, they should originate, especially in the case of polyclonal antibodies, preferably from rabbits, sheep, horses, cattle, goats or, most preferably, from sheep. The use of the nonspecific antibodies is typically done before the addition of the specific antibody.

In an especially preferred embodiment, the nonspecific antibodies originate from a different animal than the specific antibody. Specific and nonspecific antibodies differ also by their so-called "constant region" $F_c$. This permits a subsequent immunochemical reaction with a secondary antibody, which recognizes certain species-specific sections in the constant region of the specific detecting antibody. In the foregoing immunochemical detection of the specific antibody, naturally this must not originate from the same animal species as the antibody needed for saturation.

Saturation with a nonspecific antibody is conceivable both in the case of direct as well as in the case of indirect determination of the binding of the specific antibody.

In another preferred embodiment, monoclonal or polyclonal antibodies or $F_{ab}$ fragments thereof are used for the determination of the contained substances. For a very rapid determination, cost-effective polyclonal antibodies are preferred, while the monoclonal antibodies are especially suitable if it is desired to detect exactly-defined cross-reactivities, for example, in the sense of group selectivity. $F_{ab}$ fragments are not suitable for coupling with certain immunomarkers, but also they have a comparatively low tendency to bind nonspecifically.

When using antibodies in analysis, highly selective, simultaneously strongly binding antibodies are distinguished from weakly selective, simultaneously weakly binding antibodies (the corresponding antibodies can be selected with the hybridoma technique). While a high selectivity of antibodies is ideal for the identification of a given substance—here a given substance contained, for example, an allergen—a not very selective antibody has the advantage of considerable "cross-reactivity," that is, it binds to similar structures with a similar binding constant.

The analytical sensitivity can be adjusted with the aid of the binding strength of the antibody. This is important for the practical use of a test because the degree of sensitivity needed depends on the given requirements.

In another preferred embodiment, the antibody is isolated by immunostimulation of mammals, especially goats, sheep, pigs, rats, horses, rabbits, guinea pigs, poultry, cattle, and/or mice. This is done by injecting into the mammal a certain, optionally allergenic component or epitope of a certain, optionally allergenic component with sufficient antigenic properties. The mammal answers to this foreign antigen with an immune reaction, which leads to the formation of antibodies. In this process, polygonal antibodies against the foreign antigen can be obtained.

A monoclonal antibody used according to the invention (for example, an antiallergen antibody) may be produced according to any suitable method. For example, spleen cells of immune-stimulated mice may be fused after reaching the optimum antibody titer with in vitro raised myeloma cells in polyethylene glycol and then raised on a HAT medium. In this medium, only the so-called hybridoma cells from spleen and myeloma can survive. In order to isolate suitable clones which produce the antibodies, the individual clones are checked for their immunoglobulin production and the producing clones are raised either preferably in vitro or, optionally, in mice. For further details on the production of monoclonal antibodies, reference is made to "Monoclonal Antibodies, Hybridomas: A new dimension in biological analyses, Kennet et al., Plenum Press, New York, 1980", "Antibodies, A Laboratory Manual, Harlow & Lane, Cold Spring Harbor Laboratory Press, 1988" and "Peters, F. H., Baumgarten, H., Monoclonal Antibodies, 2nd Edition, Springer-Verlag, Berlin-Heidelberg-New York, 1990", the respective disclosures of which are incorporated herein by reference. The resulting monoclonal antibodies have the property of originating from one cell and thus all have the same specific antibody properties, that is, they all recognize the same epitope.

Antibodies according to the invention can be isolated and purified according to any suitable method (see Antibodies, A Laboratory Manual, Harlow & Lane, Cold Spring Harbor Laboratory Press, 1988), including but not limited to the following methods: peptide and protein column chromatography, HPLC, including "reverse phase" HPLC, protein isolation on protein A or protein G columns, and all conceivable combinations of these methods.

In a preferred embodiment, the antibodies for the detection reaction are marked in such a way that their association with the allergen or foreign substance becomes visible, such as by marker molecules which serve to mark the specific detecting antibody. In this way, it is possible to determine the presence of the antigen recognized by the antibody qualitatively and/or quantitatively. This is possible in one way by direct marking of the antibody directed against an optionally allergenic contained substance (for example, by fluorescence marking, radioactive marking, or covalent coupling to a suitable marker enzyme) or indirectly, through a second anti-anti-antigen-antibody directed against the specific anti-antigen-antibody, which can also be marked by any method described above or by any other suitable method. A method in which the detecting antibody (monoclonal, polyclonal, or $F_{ab}$ fragment) or a secondary antibody directed against the detecting antibody is marked by the fluorescence method, is preferred. In this case, upon irradiation with a corresponding excitation wavelength, the detection can be done directly on a visual basis.

The fluorescing molecule can be bound to the antibody used according to the invention through primary valences or secondary valences. In the corresponding optical excitation, the antibody then gives a fluorescence signal and thus indicates the presence of the particular antigen.

Examples of suitable fluorescent probes includes 1-anilino-8-naphthalenesulfonate, 1-dimethylaminonaphthalene-5-sulfonyl chloride, fluorescein isothiocyanate, rhodamine and its derivatives and donor-substituted oxindigo (Angew. Chem. 1996, 108, 1090–1093), which are bound to the antibodies through primary or secondary valences.

As an alternative to fluorescence marking, in another preferred embodiment, marking of the anti-antigen-antibody is performed with radioactive isotopes. Preferred is the use of a γ-source, $^{125}I$, with which a phenol group of a tyrosine of an antibody according to the invention is marked. In this case, a scintigram would be prepared for the detection of the antigen to be determined. However, the use of a soft β-source, such as $^3H$, $^{35}S$ or $^{14}C$, is possible.

Moreover, in another embodiment, the marker molecule can be an enzyme which reacts with a substrate in a quantifiable manner. The enzymes are bound to the antibodies by covalent binds. Typically, alkaline phosphatase or peroxidase, especially horseradish peroxidase, which then can be detected, for example, by oxidation with $H_2O_2$ in the presence of tetramethylbenzidine, whereupon a blue dye is formed, can be used, or double enzyme systems in which the product of the first enzyme reaction (of the enzyme that is covalently bound to the antibody), is further reacted in a second subsequent enzyme reaction and only the product of the second reaction is detected can be used.

Substances contained in fibers or polymers, which are proven to be antigens with the aid of antibodies may be considered allergens or foreign substances, include textile dyes, textile additives, and/or their accompanying substances and the fibers or polymers themselves. In an especially preferred embodiment of the invention, therefore, the foregoing contained substances are detected with the aid of antibodies.

Although the foregoing substances are harmless to the majority of the population, they represent a considerable health hazard to allergic persons under certain circumstances. Since one cannot expect that, because of such a small group of affected persons these substances would be prohibited, over the long term, a permanent need arises from this for a cost-effective analytical method which can be used by allergic persons in a routine manner when purchasing each new piece of clothing.

"Textile aids or their accompanying substances" are defined herein as those substances which are needed during the textile processes (recovery and manufacture of textile fibers, processing, finishing, and packaging), and include but are not limited to the following examples: antistatic agents, antimicrobial substances, optical brighteners, agents protecting against insect damage, finishing agents, impregnating agents, stabilizers, stiffening agents, and agents for textile coating.

Dyes are also used in textile processes. They are generally used together with dye solvents and dispersing agents. Dyes include reactive, direct, vat, sulfur, cationic coupling, and dispersion dyes.

Other contained substances that may be allergens or substances that are harmful to health in some other way, may be applied onto the fibers either during the dyeing process or are used as textile aids. Examples are pentachlorophenol (PCP), o-phenylenediamine, p-phenylenediamine, dimethyloldihydroxyethyleneurea, dimethylolethyleneurea, dimethyloltriazone, and dimethylolurea.

According to the invention, especially preferably dyes contained on textile fibers or polymers are detected. Their detection with the aid of an antibody and, preferably, fluorescence markers requires a number of specific boundary conditions, as set forth below:

Firstly, the excitation energy of the fluorescent marker is also emitted again as fluorescent light, but is not transferred to the dye, and is thus lost (fluorescence quenching). An excitation wavelength of the fluorescent marker may be longer than the absorption wavelength of the dyes to be detected, so that energy transfer is not possible. However, such a method would greatly limit the number of detectable color tones and would completely fail in the case of turquoise-colored dyes, because these absorb at the long-wavelength limit of the visible region so that a fluorescent marker that would be suitable for this would have to fluoresce not in the visible but in the NIR region, requiring detection with a machine. A suitable method is to position the fluorescence marker at a sufficient distance from the dye chromophores, namely at a distance greater than the Förster radius, which can be set as a minimum of 30 Å so that, as a consequence, no fluorescence quenching can occur by energy transfer. A sufficient distance would be given already if the dye is not adjacent to the binding arm of the antibody, but is in farther removed antibody structural regions. Suitable linking methods are available for this.

A second, important point concerns the selection of a suitable fluorescence wavelength for the fluorescent antibody system. The spectral region available for this is highly limited by the usual treatment, for example, of textile fibers with optical brighteners (textile pretreatment and detergent additives), which fluoresce in the violet-to-blue region so that a fluorescence maximum can be set at approximately 435 nm. Since a sufficient safety distance would have to be observed from the emissions of the brightener, the green spectral region must also be avoided in these cases. Therefore, the fluorescent markers preferably fluoresce in the yellow region, the orange-red region, or the red region.

Preferably, however, the long-wavelength red spectral region is also to be avoided because the sensitivity of the human eye or that of photomultipliers decreases greatly at these wavelengths. Therefore, especially preferably, the long-wavelength limit of fluorescence is between 650 nm and 700 nm.

For fluorescence immunodetection with a machine, spectral decomposition would be a suitable method to separate the fluorescent antibody signal from the fluorescent background, which is caused by the optical brightener. For visual evaluation of the immunofluorescence, the fluorescent background produced by the optical brightener is also disturbing. This can be filtered out with a color filter with a long-wavelength spectral edge ("edge filter") at 450 to 500 nm. However, for a simple routine analytical method, observation through a filter, preferably through a yellow plastic film is sufficient.

Should the detection of the immunofluorescence take place with high sensitivity, then all fluorescent background of the fibers or polymers, caused by the production or by impurities, will disturb the process. This problem can essentially be eliminated by the use of fluorescent markers with an increased Stokes shift. Such an increase of the Stokes shift follows from special structural requirements. These requirements are generally not fulfilled by occasional available substances because usually a normal Stokes shift is found therein. The fluorescence of the markers can be separated with the usual optical filters from the fluorescence of the background, as is known in the art.

In one preferred embodiment, among the textile dyes, dispersion dyes which typically have a potentially allergenic character are detected according to the method. Dyes that may be detected according to the invention include but are not limited to the following: DISPERSION-BLUE 124, DISPERSION-BLUE 3, DISPERSION-BLUE 7, DISPERSION-YELLOW 3, DISPERSION-YELLOW 9, DISPERSION-ORANGE 3, DISPERSION-ORANGE 76, DISPERSION-RED 1, and metholmelamine.

In another preferred embodiment, among textile dyes, dyes with an azo group ("azo dyes"), which can also have a potentially allergenic character, are detected.

Moreover, the analysis of azo textile dyes has assumed special importance because of the prohibition of certain such dyes by governmental agencies (e.g., the 2nd to 4th Amendment of the Commodities Regulation). Since the prohibition may be extended to additional azo dyes, generally there is a high demand for analytical capacity for the identification of such dyes. Firstly, for a detection method, it is necessary that it allows the identification of certain azo dyes in colored textiles and, on the other hand, methods are needed with which the azo group can be directly detected as a substructure. The latter is of special importance because more than 10,000 different azo dyes are known. The development and application of special methods of determination for each of these azo dyes would mean an extraordinarily high technical demand. Another aggravating factor is that not only are new azo dyes designed and synthesized without any problem, but in industry, frequently azo dyes are also used as reactive dyes, which are bound covalently to the fiber and therefore cannot be extracted or otherwise removed. Identification of such fiber-dye conjugates requires breaking of chemical binds for conventional methods of determination, which would bring about additional uncertainties in the analytical method.

The development of a universal analytical method for the identification of azo dyes is therefore highly desirable. Thus, methods are preferred in which the antibodies show a high selectivity toward partial molecular structures of azo dyes. According to the invention, this is possible by the use of antibodies against the inherent azo group of azo dyes as an antigenic substance. Such antibodies that are used according to the method thus represent universal reagents for azo dyes.

The sensitivity for the detection of the azo group can be adjusted with the binding strength of the antibody. This is important for the practical use of a testing system because different degrees of sensitivity are necessary depending on the requirements. Then, the class of azo dyes can be detected via cross-reactivities using one or a few antibodies. However, depending on the requirements, it is favorable to use either only one antibody and take into consideration differences in the cross-reactivities, or to level out the differences by the use of several antibodies, which take into account the specific, slightly different, binding relationships around the azo group.

In another preferred embodiment, antibodies are used which, in addition to the azo group, require other molecular parts as a component of the recognition structure, the epitope. These additional antigenic molecular structures are then characteristic for individual azo dyes or for subgroups of azo dyes. Thus, certain azo dyes can be identified and determined quantitatively with such antibodies.

In an especially preferred embodiment, for this purpose, the antibodies are coupled with a fluorescent marker through primary or secondary valences. Preferably, these are markers with a yellow, orange-red, or red emission signal. The fluorescent markers can be bound directly to the detecting antibody or to a secondary antibody which is directed against the detecting antibody. In order to produce a large distance between the chromophore and fluorescent marker, the marker is in a region which is away from the paratope of the antibody.

The immunochemical detection method of azo dyes on textile fibers according to the invention is necessary because certain azo dyes are on a prohibition list. Moreover, the methods according to the invention can also be used very generally for the detection of substances that give rise to concern about health, in fibers or polymers, especially in textiles. However, the methods according to the invention can also be used for other problems, such as for the identification of certain substances contained in polymers or fibers for the detection of their origin. Application of the method according to the invention in the criminological area is also possible.

We claim:

1. A method for detecting a presence of a substance contained in a substrate, which substrate is selected from the group consisting of textile fibers, natural polymers, and synthetic polymers, said method comprising the steps of:

(a) directly contacting the substrate and the substance therein with first, specific antibodies that specifically bind to said substance; and, (b) detecting or quantitatively determining the first antibodies bound to said substance as an indication of the presence of said substance.

2. The method of claim 1 wherein prior to step (a) the substrate surface is saturated with second, non-specific antibodies which do not specifically bind to an epitope of the substance to be detected.

3. The method of claim 2 wherein the nonspecific antibodies originate from a species different from that from which the specific antibodies originate.

4. The method of claim 1 wherein said specific antibodies are selected from the group consisting of polyclonal antibodies, monoclonal antibodies, $F_{ab}$ fragments derived from polyclonal antibodies, and $F_{ab}$ fragments derived from monoclonal antibodies.

5. The method of claim 1 wherein said specific antibodies are obtained from an animal selected from the group consisting of mice, rats, rabbits, guinea pigs, sheep, goats, cattle, horses, and poultry.

6. The method of claim 1 wherein said specific antibody is marked with a marker selected from the group consisting of radiochemical markers, enzymatic markers, and fluorescence markers.

7. The method of claim 1 wherein the substance to be detected with antibodies is an antigen selected from the group consisting of textile dyes, textile aids, byproducts of textile dyes, byproducts of textile aids, and components of the substrate.

8. The method of claim 1 wherein the substance to be detected is a dispersion dye.

9. The method of claim 1 wherein the substance to be detected is an azo dye.

10. The method of claim 9 wherein the antibody is specific for the azo moiety of the dye molecule but not for other characteristic parts of the dye molecule.

11. The method of claim 9 wherein the specific antibody is specific to the azo moiety of the dye molecule and to at least one other characteristic part of the dye molecule.

12. The method of claim 1 wherein a fluorescence marker with yellow fluorescence, orange-red fluorescence, or red fluorescence is coupled through primary or secondary valences to a structural region of the specific antibody which is distal from a paratope of the specific antibody.

13. The method of claim 1 wherein said substrate comprises a material selected from the group consisting of cotton, animal hair, silk, jute, sisal, hemp, flax, and converted products thereof.

14. The method of claim 13 wherein said substrate is selected from the group consisting of wool, horsehair, viscose fibers, nitrate silk, and copper rayon.

15. The method of claim 1 wherein said substrate comprises a synthetic material selected from the group consisting of polyvinyl chloride, cellulose acetate, polycarbonates, polyamides, polyurethanes, polyimides, polybenzimidazoles, melamine resins, silicones, polyesters, polyethers, polystyrene polymethyl methacrylate, polyethylene, polypropylene, polyvinyl acetate, polyacrylonitrile, polybutadiene, polychlorobutadiene, polyisoprene, and copolymers thereof.

* * * * *